United States Patent
Dall

(10) Patent No.: US 6,258,092 B1
(45) Date of Patent: Jul. 10, 2001

(54) CORTICAL BONE SCREW

(76) Inventor: Vagn Erik Dall, 36 Bray Bank, Old Mill Lane, Bray, Maidenhead, Berkshire (GB), SL6 2BG ( * ) Notice: Subject to any disclaimer, the term of this patent is extended or adjusted under 35 U.S.C. 154(b) by 0 days.

(21) Appl. No.: 09/214,323

(22) PCT Filed: Jul. 3, 1997

(86) PCT No.: PCT/GB97/01785

§ 371 Date: Sep. 13, 1999

§ 102(e) Date: Sep. 13, 1999

(87) PCT Pub. No.: WO98/01079

PCT Pub. Date: Jan. 15, 1998

(30) Foreign Application Priority Data

Jul. 3, 1996 (GB) .................................................. 9613916

(51) Int. Cl.[7] .................................................. A61B 17/86

(52) U.S. Cl. .................................. 606/73; 606/72; 606/71

(58) Field of Search .................................. 606/72, 73, 60, 606/65, 69, 70, 71

(56) References Cited

U.S. PATENT DOCUMENTS 3,550,668 * 12/1970 Coyle .
5,167,664 * 12/1992 Hodorek .................................. 606/73

* cited by examiner

Primary Examiner—David O. Reip
(74) Attorney, Agent, or Firm—Wallenstein & Wagner, Ltd.

(57) ABSTRACT

A cortical bone screw assembly which includes a threaded shaft and a nut. The nut includes a radially resilient body with a normal internal diameter less than the pitch diameter of the shaft thread and accommodates radial expansion of the body to allow translational movement of the nut along the shaft over the thread, but precludes translational movement when the radial expansion is prevented

18 Claims, 2 Drawing Sheets

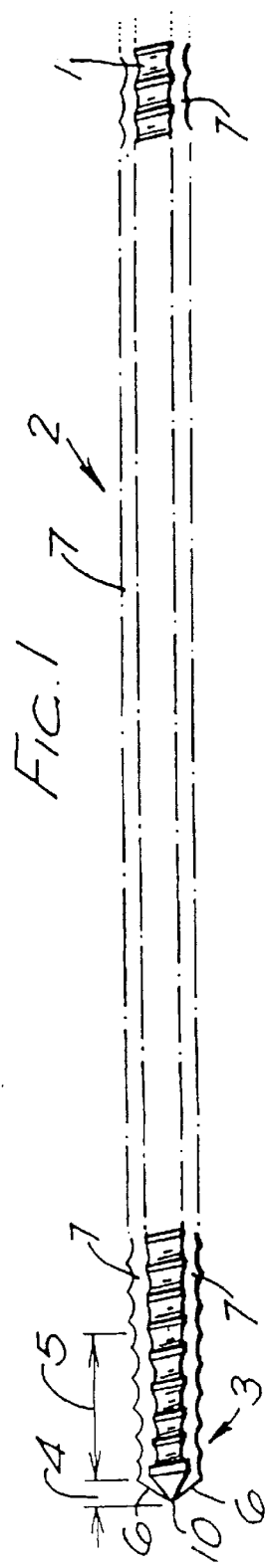
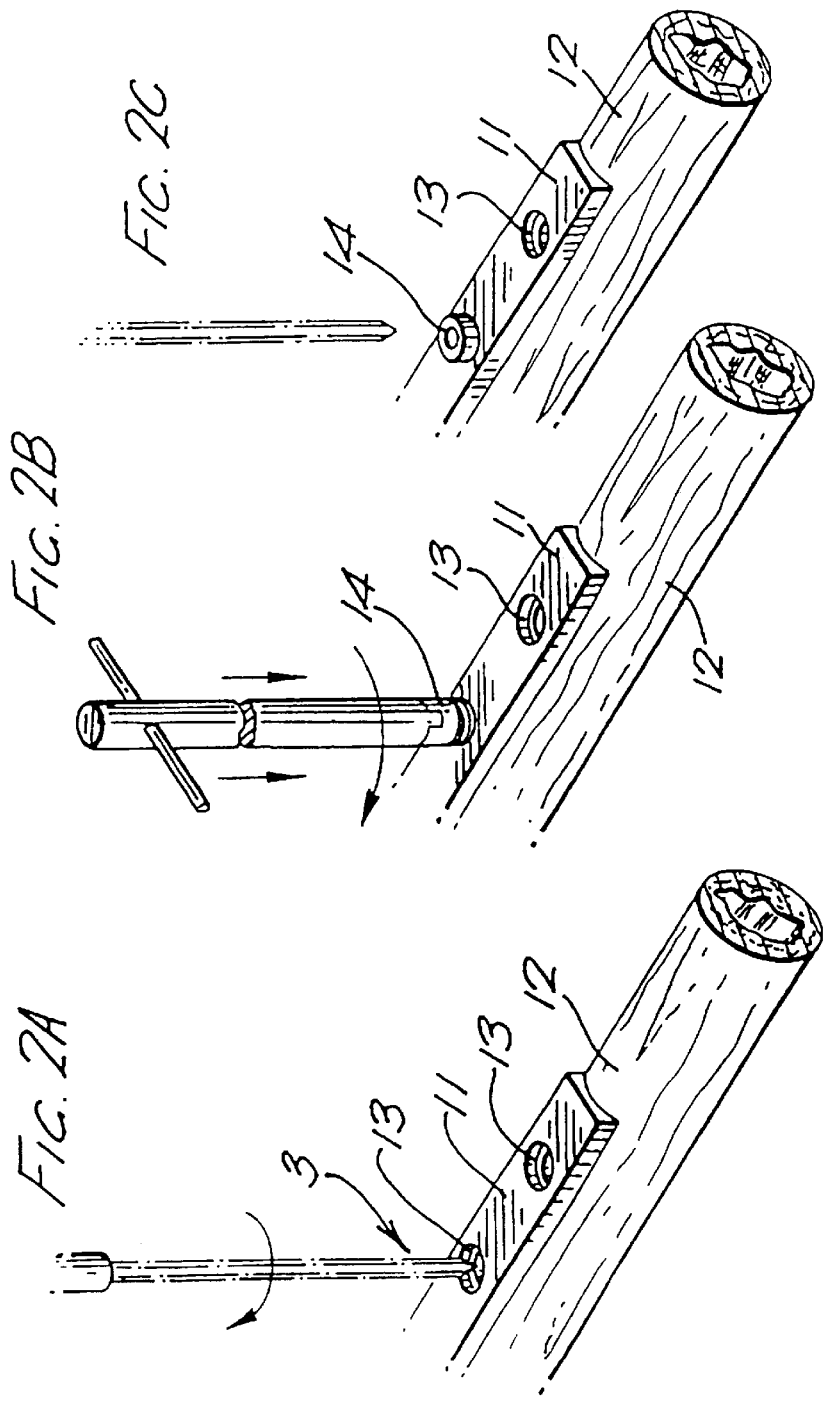

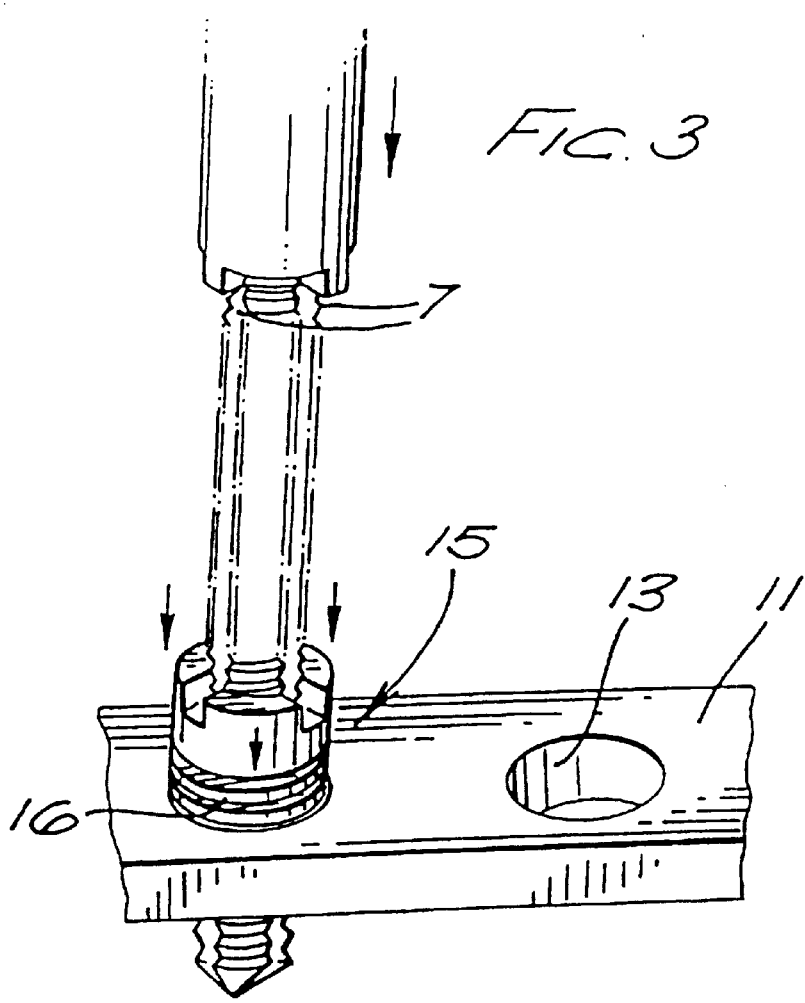
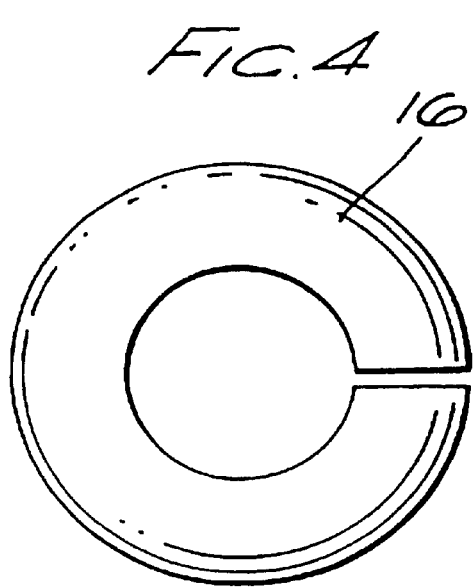
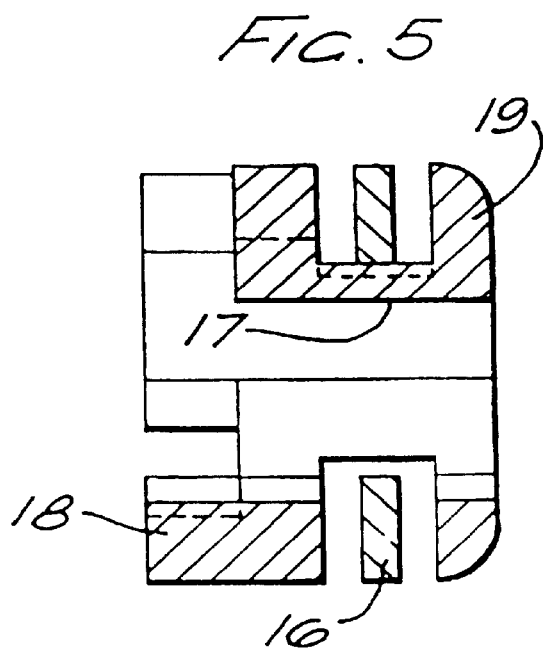

CORTICAL BONE SCREW

This invention relates to cortical bone screws, and to methods of using such screws in securing plates and the like to bones in the conduct of surgical operations.

Traditionally, bone screws are provided in a variety of different lengths, and are broadly similar in appearance to conventional wood screws. Their use is a cumbersome procedure which requires the careful selection of a screw in each case. The present invention is directed at a bone screw which avoids this selection procedure by being adaptable to a wide range of lengths of hole. By this means, there is no longer any need to keep a range of bone screws for a surgeon's use. In each case the same screw is selected.

According to the invention a bone screw assembly for use in surgical operations comprises a threaded shaft and a nut therefor which nut includes a radially resilient body with a normal internal diameter less than the pitch diameter of the shaft thread, and accommodates radial expansion of the body to allow translational movement of the nut along the shaft over the threads thereof but precluding such translational movement when radial expansion of the body is prevented. Thus, such translational movement of the nut is possible over an exposed length of shaft. However, when the nut is in a restricted volume which prevents expansion of the resilient body, the nut is bound to the shaft by the body. The assembly of the invention is adapted for use in circumstances where final axial movement of the nut is by rotation within a socket to secure the socket or the body in which it is formed, in place.

In assemblies of the invention, portions of the resilient body will upon radial expansion, project beyond the lateral boundary defined by the nut. Thus, this lateral boundary defines the cross-section required to prevent the resilient body from expanding to pass over the shaft thread in translational axial movement therealong. The resilient body is typically received in an annular groove formed in the nut, and is typically a split ring of resilient material. The housing itself may be formed in two parts to facilitate installation of the resilient body.

Because the nut in the assembly of the invention is adapted to be received in a restricted volume, conventional turning mechanisms that engage the peripheral surface thereof are inappropriate. In assemblies according to the invention therefore, the nut is adapted for coupling to a turning device engaged with its exposed axial end. Typically this is accomplished by the provision of castellations on the nut end, and a turning device may be provided which fits over the exposed length of screw shaft to engage the castellations. This has the advantage of providing for alignment of the turning device with the nut, and in certain variants of the invention the turning device may include a mechanism for severing the exposed length of shaft at the end face of the nut when the nut has been sufficiently tightened.

The restricted volume into which nuts and assemblies of the invention are adapted to be received is typically defined by a socket having an opening with an internal cross-section corresponding to a lateral boundary defined by the nut. The socket can be a sleeve which is axially movable relative to the nut to be engaged therewith when translational movement of the nut along the shaft is to be prevented. Such a socket can be adapted to be received in a plate for example to be secured to a bone surface, enabling the screw to be used to hold the plate against the surface. However, in preferred embodiments of the invention the socket is itself formed as part of the plate whereby the nut is received directly in an opening in the plate having a stepped cross-section. As the nut is received in the larger cross-section of the opening, which prevents radial expansion of the resilient body, the nut can then be turned to engage the step in the opening, and thereby clamp the plate to the bone surface.

While the use of bone screw assemblies according to the invention will normally be in conjunction with a pre-drilled and tapped hole in the bone, the shaft of the screws can be made with a self-tapping section at the end which is driven into the bone. In preferred embodiments, the self-tapping section has a conical cutting end with a plurality of flutes extending axially therefrom across the shaft thread. This enables the screw to be used not only to tap the thread in the hole formed in the bone, but also in the formation of the hole itself. For this purpose, the cutting end may be formed with a plurality of edges with different radii. This enables the hole to be cut progressively at different radii to reduce the generation of heat as the hole is drilled.

Flutes in the surface of the screw shaft provide a convenient means by which rotation of the nut on the shaft can be prevented. Thus, the nut may be formed with inwardly projecting pillars for receipt in the flutes, and around which the resilient body extends. In this variant, translational movement of the nut on the shaft is to some extent controlled, and when this is prevented by the nut entering the hole in the plate the rotational "lock" is particularly secure.

Bone screws according to the invention are typically metallic, usually being formed in corrosion resistant alloys. However, in some circumstances the shaft and/or the nut can be formed in plastics materials, and this can be of particular value where a degree of flexibility is desired.

An embodiment of the invention will now be described by way of example and with reference to the accompanying schematic drawings wherein:

FIG. 1 shows a side view of the shaft of a bone screw assembly in accordance with one embodiment of the invention;

FIGS. 2a, 2b and 2c illustrate the use of an assembly according to the invention in securing a plate to a bone surface;

FIG. 3 is an enlarged perspective view of an assembly in accordance with the invention with the nut shown at the point of entry into an opening in a plate;

FIG. 4 is an axial elevation of a radially resilient body for use in an assembly according to the invention; and FIG. 5 is a cross-section through a two piece nut incorporating the resilient body of FIG. 4.

The shaft shown in FIG. 1 has one plane end 1; a main threaded section 2; and a cutting and self-tapping end section 3. The end section 3 has a cutting end 4 and a conical tapping section 5. The cutting section 4 has three edges 6 of different radii which are progressively used to cut the full diameter of the hole as the shaft is driven into a bone section. Material removed by the cutting edges 6 passes into adjacent flutes 7 extending axially through the external thread of the shaft. The extreme tip of the shaft comprises a pointed tip 10 for accurate location when the cutting exercise is started. As shown the flutes 7 extend the entire length of the shaft.

In FIGS. 2 the use of an assembly according to the invention is illustrated. As shown in FIG. 2a, a plate 11 is located over a bone section 12 in the desired relative orientation. The plate 11 has holes 13, each with a stepped cross-section. The small cross-section is in juxtaposition with the bone section 12. As a first step, the end section 3 of the bone screw shaft of FIG. 1 is first driven into the bone section 12 through a hole 13. As noted above, it is either fitted into a hole already prepared in the bone, or itself acts as the drill making the initial hole. With the shaft in place, a nut 14 having a resiliently flexible locking ring as described below, is fitted over the shaft and driven down the shaft, without rotation, into juxtaposition with the plate 11 over the respective hole 13. In order to traverse the threads of the shaft, the locking ring is cyclically distorted, and portions of the locking ring traversing the thread project beyond the circular boundaries of the nut 14. The circular boundary of the nut complements the internal diameter of the large cross-section of the hole 13, and as the nut enters the hole the body portions can no longer project beyond the nut boundary. At this point, and using a turning device disposed over the exposed shaft, the nut is turned to tighten against the step in the hole 13 in the plate 11, securing and clamping the plate 11 against the bone section 12. The turning device is then removed, and the exposed length of screw shaft cut at its junction with the exposed face of the nut. By proper selection of the dimensions of the various components, the exposed surfaces of the plate 11, nut 14, and cut shaft can be substantially flush, leaving a smooth surface for further treatment as necessary.

Critical of course to the successful practice of the technique described above with reference to FIGS. 2 is the nut 14. A suitable construction therefor is now described in a little more detail and with reference to FIGS. 3 to 5.

As shown in FIG. 3, the nut 14 consists of a main cylindrical housing 15 bearing a resilient body in the form of a split ring 16 or a spring section or length of resilient wire bent to engage the thread in its unflexed shape. The ring 16 extends around three pillars 17 connecting upper (18) and lower (19) parts of the housing 15. These pillars 17 are disposed in correspondence with the flutes 7 on the screw shaft, enabling the nut 14 to translate axially along the shaft, but preclude relative rotation. The upper housing part 18 is formed with castellations to receive a turning device, and the lower housing part 19 is formed with bevelled edges to facilitate location in the respective hole 13 in the plate 11.

The split ring 16 has a normal, unflexed inner diameter less than the pitch diameter of the screw shaft, but normally greater than the trough diameter. Thus, as the nut 14 translates axially along the screw shaft, the ring 16 is cyclically distorted outwardly as it traverses the thread peaks. The normal, unflexed outer periphery of the split ring 16 substantially corresponds to the peripheral boundary of the nut housing 15. The larger cross-section in the respective hole 13 substantially corresponds with that of the nut housing 15, and thus when the nut enters the hole, the split ring 16 is no longer able to expand and the nut is effectively locked on the shaft. The turning device is then applied to the castellations to finally tighten the bone screw, and clamp the plate 11 against the bone section 12.

What is claimed is:

1. A cortical bone screw assembly comprising a threaded shaft and a nut therefor, the nut including a radially resilient body with a normal internal diameter less than the pitch diameter of the shaft thread, and accommodates radial expansion of the body to allow translational movement of the nut along the shaft over the thread thereof; and an element formed with an opening within a socket having an internal cross-section corresponding to the lateral boundary of the nut, wherein portions of the body project beyond the lateral boundary of the nut upon radial expansion to pass over the shaft thread in said translational movement, the socket being adapted to receive the nut and thereby confine the body portions to the dimensions of the lateral boundary of the nut and prevent translational movement of the nut over the shaft.

2. An assembly according to claim 1 wherein the body (16) is received in an annular groove formed in the nut (14).

3. An assembly according to claim 2 wherein the body is a split ring of resilient material.

4. An assembly according to claim 3 wherein the resilient material is a spring steel.

5. An assembly according to claim 3 wherein the resilient material is a plastic material.

6. An assembly according to claim 2 wherein the nut is formed with means for coupling with a turning device.

7. An assembly according to claim 6 wherein the coupling means comprises sockets in a face of the nut for receiving the prongs of a turning device.

8. An assembly according to claim 2 including means for preventing rotation of the nut on the shaft.

9. An assembly according to claim 2 wherein the element is a plate to be secured to the surface of a bone, the socket being formed in the remote face of the plate such that the nut has to be turned on the shaft to press the plate against the bone surface.

10. An assembly according to claim 1 wherein the body is a split ring of resilient material.

11. An assembly according to claim 10 wherein the resilient material is a spring steel.

12. An assembly according to claim 10 wherein the resilient material is a plastic material.

13. An assembly according to claim 1 wherein the nut is formed with means for coupling with a turning device.

14. An assembly according to claim 13 wherein the coupling means comprises sockets in a face of the nut for receiving the prongs of a turning device.

15. An assembly according to claim 1 including means for preventing rotation of the nut on the shaft.

16. An assembly according to claim 15 wherein the shaft is formed with axially extending flutes (7) on the surface thereof, and the nut is formed with inwardly projecting pillars (17) for receipt in the flutes (7), and around which the resilient body (16) extends.

17. An assembly according to claim 1 wherein the element is a plate to be secured to the surface of a bone, the socket being formed in a remote face of the plate such that the nut has to be turned on the shaft to press the plate against the bone surface.

18. A method of securing a plate to a bone surface with a cortical bone screw having a threaded shaft, the plate having an opening therethrough with a stepped cross-section, the method comprising:

locating the plate on the bone surface with a larger cross-section of the opening remote therefrom;

fitting the screw to a requisite depth in the bone through the opening in the plate; fitting to an exposed end of the screw a nut including a radially resilient body with a normal internal diameter less than the pitch diameter of the shaft thread, and having an external cross-section enabling rotation thereof within the larger cross-section of the opening in the plate; and, axially translating the nut along the screw shaft to the opening in the plate and rotating the nut in the larger cross-section thereof to tighten the screw and secure the plate against the bone, and sever the exposed length of screw.

\* \* \* \* \*